(12) United States Patent
Thorne, Jr. et al.

(10) Patent No.: US 9,289,562 B2
(45) Date of Patent: Mar. 22, 2016

(54) PRESSURE ACTUATED VALVE FOR MULTI-CHAMBER SYRINGE APPLICATIONS

(75) Inventors: Gale H. Thorne, Jr., Bountiful, UT (US); Gale H. Thorne, Bountiful, UT (US)

(73) Assignee: THORNE CONSULTING and INTELETUAL PROPERTY, LLC, Bountiful, UT (US)

( * ) Notice: Subject to any disclaimer, the term of this patent is extended or adjusted under 35 U.S.C. 154(b) by 1082 days.

(21) Appl. No.: 13/068,529

(22) Filed: May 13, 2011

(65) Prior Publication Data

US 2012/0265171 A1 Oct. 18, 2012

Related U.S. Application Data

(63) Continuation-in-part of application No. 13/066,565, filed on Apr. 18, 2011.

(51) Int. Cl.
| | |
|---|---|
| *A61M 5/178* | (2006.01) |
| *A61M 5/36* | (2006.01) |
| *A61M 5/315* | (2006.01) |
| *A61M 5/19* | (2006.01) |
| *A61M 5/31* | (2006.01) |

(52) U.S. Cl.
CPC .............. *A61M 5/31596* (2013.01); *A61M 5/19* (2013.01); *A61M 5/31511* (2013.01); *A61M 2005/1787* (2013.01); *A61M 2005/3121* (2013.01)

(58) Field of Classification Search
CPC ............ A61M 5/31511; A61M 5/284; A61M 2005/3128; A61M 5/31596; A61M 2005/1787; A61M 5/19; A61M 5/2066

USPC .......... 604/45, 122, 129, 187, 218, 221, 222, 604/225, 167.03, 236, 246, 247, 249
See application file for complete search history.

(56) References Cited

U.S. PATENT DOCUMENTS

| | | | | | |
|---|---|---|---|---|---|
| 2,841,145 | A | * | 7/1958 | Epps ..................... | A61M 5/284 604/89 |
| 2,847,996 | A | * | 8/1958 | Cohen ................... | A61M 5/284 604/192 |
| 2,869,543 | A | * | 1/1959 | Ratcliff .................. | A61M 5/19 604/90 |
| 4,643,721 | A | * | 2/1987 | Brunet .......................... | 604/191 |
| 4,713,060 | A | * | 12/1987 | Riuli ..................... | A61M 5/002 604/199 |
| 5,415,648 | A | * | 5/1995 | Malay et al. .................. | 604/181 |
| 5,476,449 | A | * | 12/1995 | Richmond ...................... | 604/87 |
| 5,743,886 | A | | 4/1998 | Lynn et al. | |
| 5,785,682 | A | * | 7/1998 | Grabenkort ..................... | 604/82 |

(Continued)

*Primary Examiner* — Nathan R Price
*Assistant Examiner* — William Carpenter
(74) *Attorney, Agent, or Firm* — Gale H. Thorne

(57) ABSTRACT

Methods and apparatus are disclosed for disposing a valve within a barrel of a conventional syringe to provide, first, a mixing syringe embodiment and, second, a sequential delivery syringe embodiment. Generally, the valve divides the syringe barrel into a proximal and a distal chamber. When used for mixing, the valve is self-displaceable by expansion of decompressing matter disposed within the valve against exterior matter permitting proximal displacement of the valve independent of character of matter in the distal chamber. For sequential delivery, switching of the valve occurs after switch opening causing pressure is relieved, thereby reducing inadvertent uncontrolled flow when the valve opens. In addition, a combination mixing and flush syringe is disclosed whereby a mixing and a flush capability is provided within a conventional syringe.

8 Claims, 11 Drawing Sheets

(56) References Cited

U.S. PATENT DOCUMENTS

| | | | |
|---|---|---|---|
| 7,048,720 B1* | 5/2006 | Thorne et al. | 604/191 |
| 7,101,354 B2 | 9/2006 | Thorne, Jr. et al. | |
| 7,789,862 B2 | 9/2010 | Thorne, Jr. | |
| 2005/0245880 A1* | 11/2005 | Howlett et al. | 604/231 |
| 2009/0018496 A1* | 1/2009 | Harper | A61M 5/31596 604/89 |

* cited by examiner

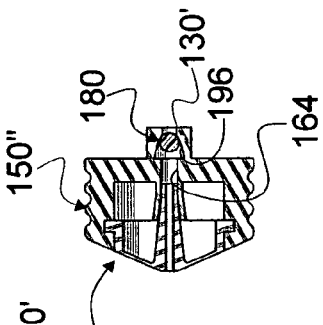
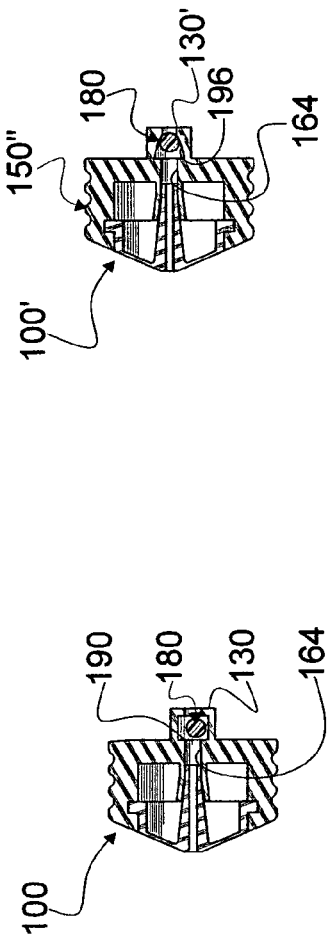
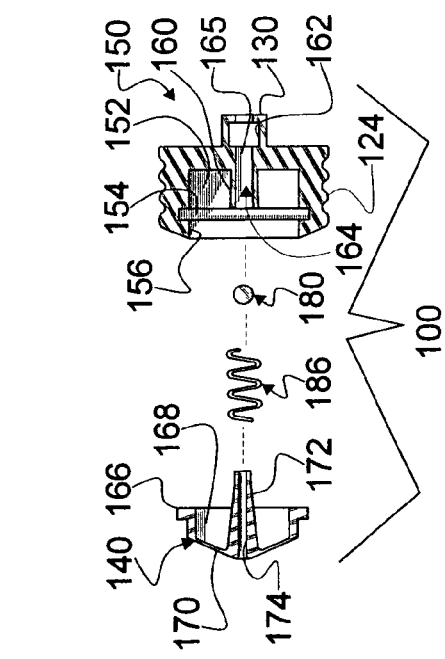
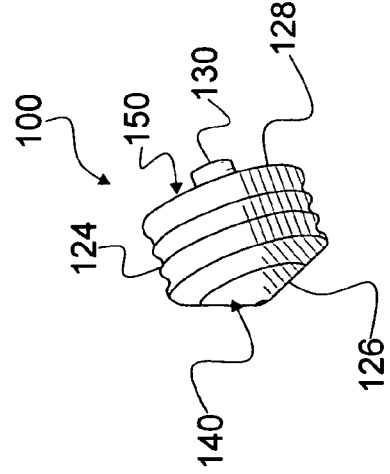
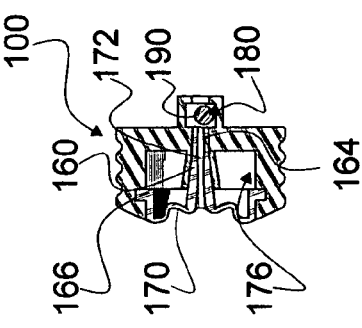

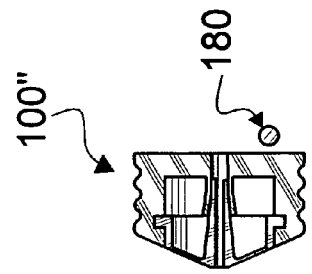
Figure 12
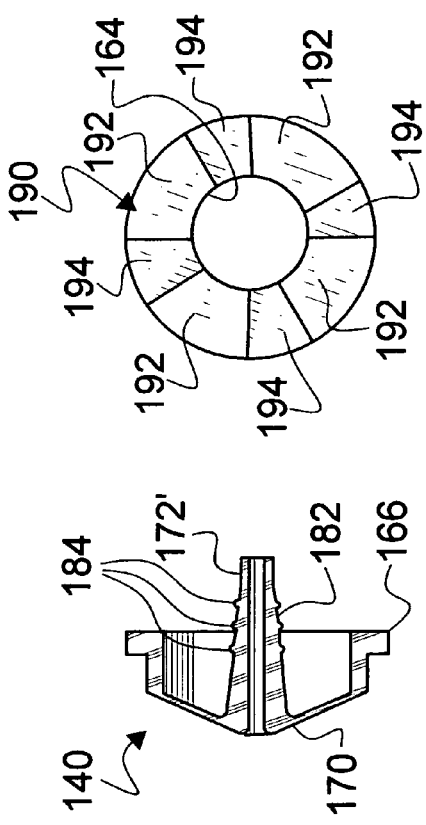
Figure 11
Figure 13
Figure 26B
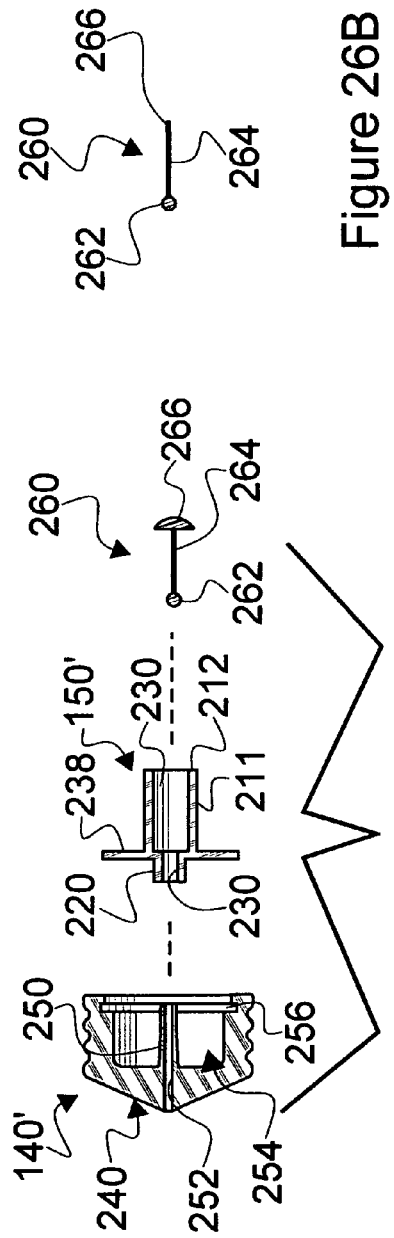
Figure 26A

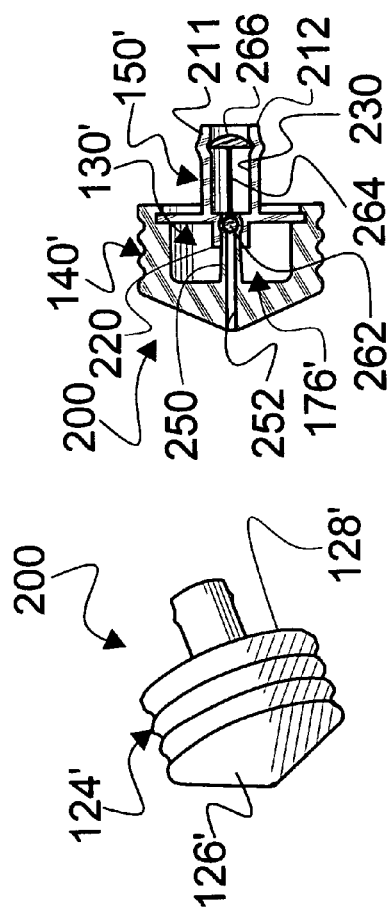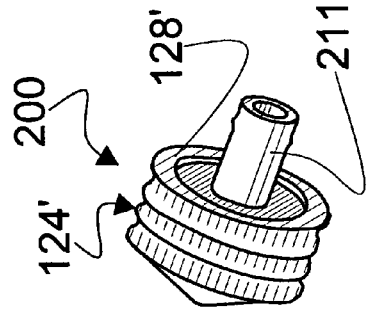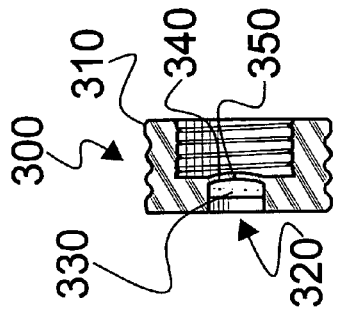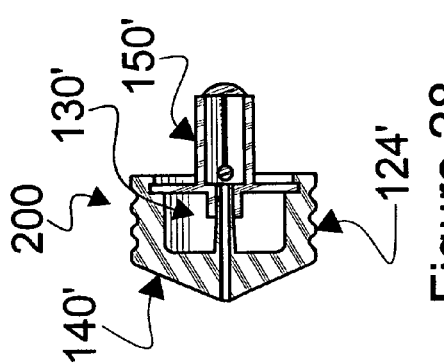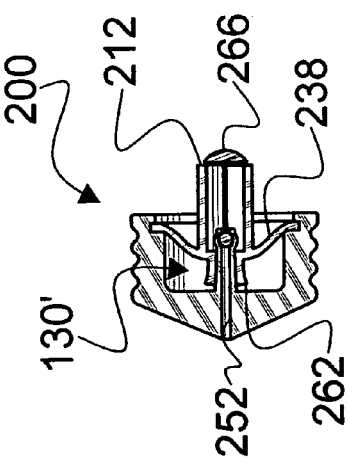

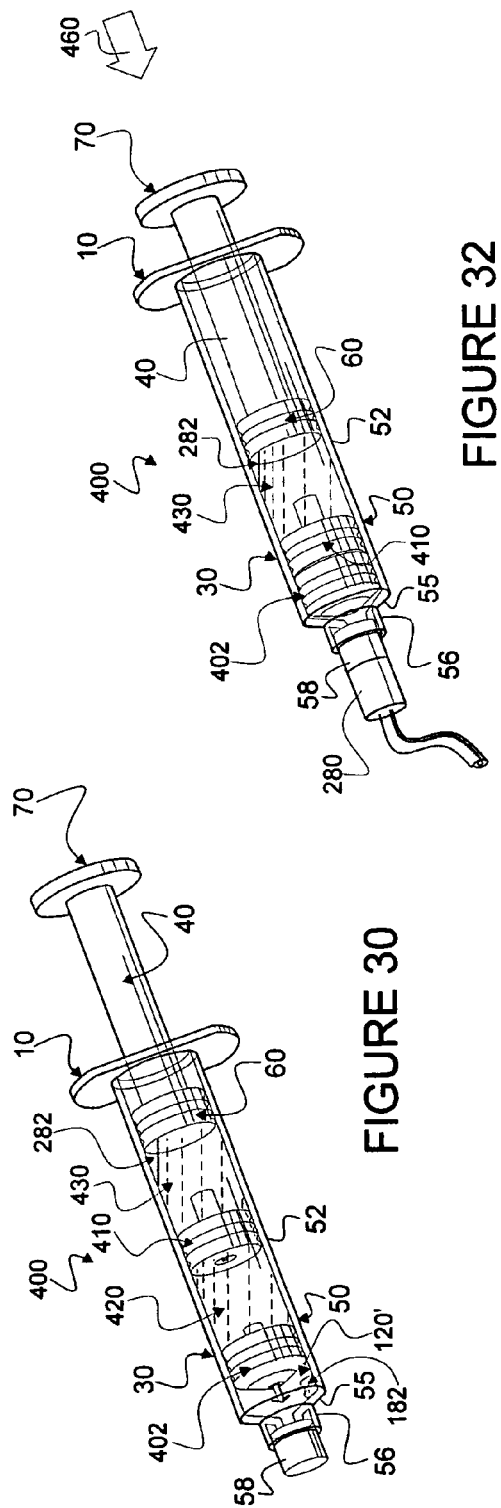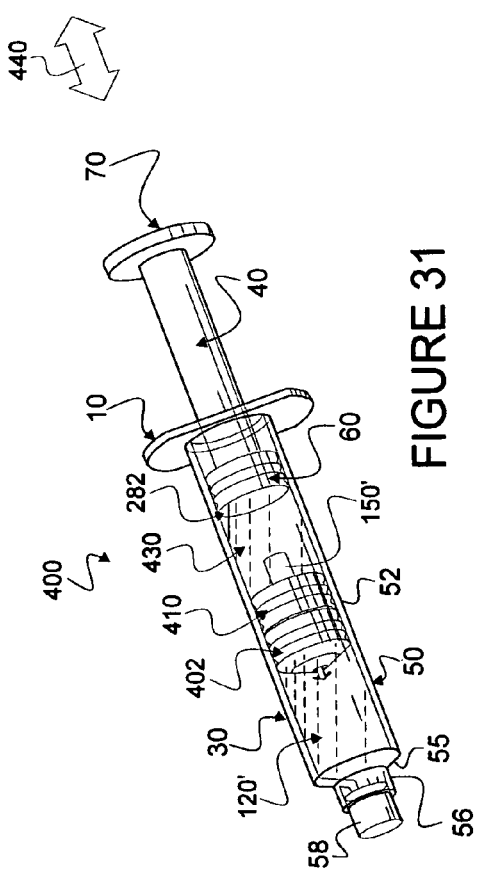

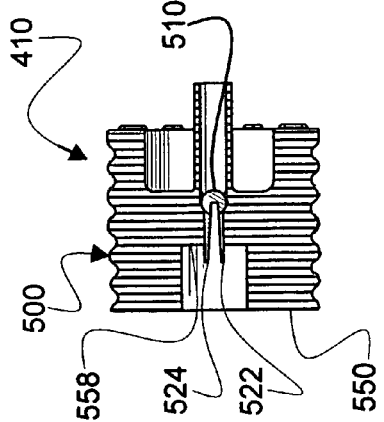
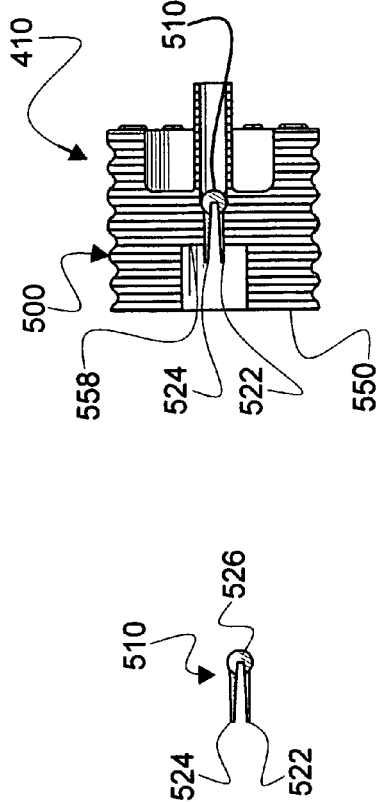
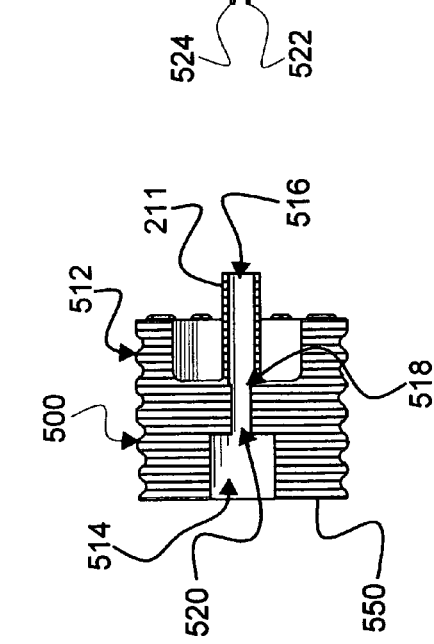
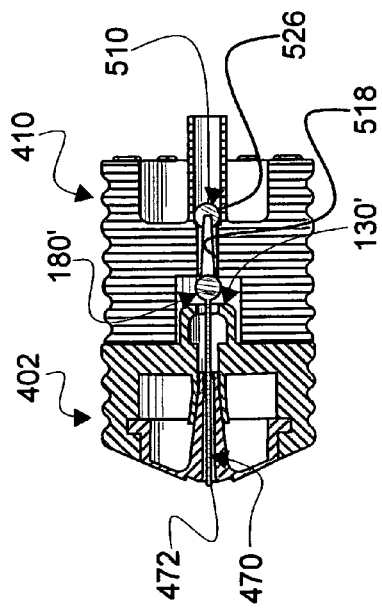
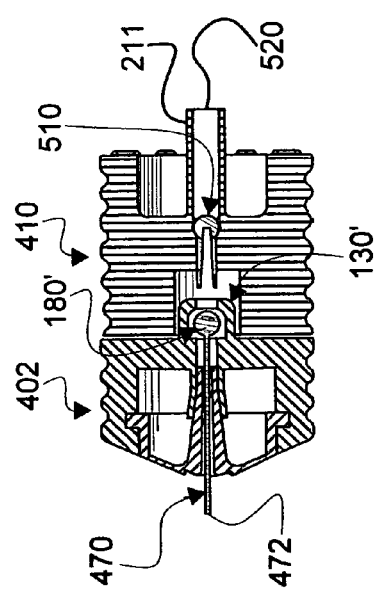

PRESSURE ACTUATED VALVE FOR MULTI-CHAMBER SYRINGE APPLICATIONS

CONTINUATION-IN-PART

This Patent Application is a Continuation-in-Part of U.S. patent application Ser. No. 13/066,565, titled MEDICAL SYRINGE PRIME AND CROSS-CONTAMINATION FREE DEVICES filed Apr. 18, 2011, by Gale H. Thorne, Jr. et al. (Thorne Application).

FIELD OF INVENTION

This invention relates to valves which are disposed in conventional medical syringes to provide either multi-chamber sequential delivery or mixing syringes or combinations of mixing and sequential delivery syringes.

BACKGROUND AND DESCRIPTION OF RELATED ART

Four U.S. Patents which are related to the instant inventions disclosed herein are U.S. Pat. No. 6,997,910 B2, titled MULTI-CHAMBER SEQUENTIAL DOSE DISPENSING SYRINGE, filed May 3, 2004 and issued Feb. 14, 2006, to Michael Wallace Howlette, et al. (Howlette 910); U.S. Pat. No. 7,048,720 B1, titled MULTI-CHAMBER DOSE DISPENSING SYRINGE, filed Nov. 22, 2005 and issued May 23, 2006 to Gale H. Thorne, et al. (Thorne 720); U.S. Pat. No. 7,789,862 B2, titled MULTI-CHAMBER SEQUENTIALLY DISPENSING SYRINGE, filed Sep. 5, 2007 and issued Sep. 7, 2010 to Gale H. Thorne, Jr. (Thorne 862); and U.S. Pat. No. 7,101,354 B2, titled MIXING SYRINGE WITH AND WITHOUT FLUSH, filed Feb. 21, 2006 and issued Sep. 5, 2006 to Gale H. Thorne, Jr. (Thorne 354) et al.

Thorne (862) and Thorne (354) disclose backgrounds, uses and basic performance requirements of sequential dispensing and mixing syringes, respectively, and are hereby cited as reference for such. While the above cited art, and other art generally related, provide a basis for commercial devices, there are some basic operational criteria which are not completely met by any prior art. These criteria include:

For Sequentially Delivery Syringes
1. Utilization of a conventional syringe barrel and a pressure actuated valve disposed within the barrel to provide for dividing space within the barrel into two disparate chambers from which sequential delivery is to be accomplished.
2. Providing a pressure actuated valve which is fully closed by a plug which, until displaced, keeps the chambers divided and totally disparate.
3. Having a two stage valve which remains closed until after being cocked by a first action and then opened by a second action whereby a first action, such as employment of a pressure to open a valve, as, for example, in the case for devices made according to Thorne (720), is not available to cause an inadvertent and uncontrolled pressure caused flow through the valve and therefrom to a patient line upon opening.
4. Actuating a valve by a tactilely or other sensibly determinable pressure disposed upon the valve within the syringe barrel, that pressure being measurably and determinably greater than inherent pressure required to overcome valve to barrel wall friction which retards valve displacement within the barrel. Both the actuating pressure and inherent pressure originating by force disposed upon a syringe plunger rod such that a valve fully disposed into contact with the end of a syringe barrel is not inadvertently opened. Opening of the valve occurring after employing a force greater than the force required to produce the inherent pressure upon the plunger rod to cock actuation of the valve and then removing the force from the plunger rod to subsequently remove pressure from the valve to open the valve as pressure is removed therefrom, thus not producing an inadvertently and uncontrollably high dispensing flow upon valve opening.

For Mixing Syringes
1. Utilization of a conventional syringe barrel and a pressure actuated valve disposed within the barrel to provide for dividing space within the barrel into two disparate chambers which are kept disparate until the valve is actuated.
2. Providing a valve which is fully kept closed by a plug, which, until opened by displacement of the plug, keeps chambers divided by the valve totally disparate.
3. Opening the valve by displacement of the plug only when pressure in the two chambers exceeds, by a predetermined pressure differential, a pressure originally contained within the pressure actuated valve.

The instant invention disclosed herein, in appropriate embodiments, meets all of the above specified criteria.

DEFINITION OF TERMS

Following is a brief list of clarifying definitions for terms used in this Application:

assembly n: a device which is made from at least two interconnected parts barrel n: a cylindrical elongated portion of a conventional syringe which is substantially of constant diameter along a long axis of the syringe, open on one end to receive a plunger tip and plunger rod assembly used for displacing fluid within the barrel and partially closed at an opposite end except for an orifice or portal through which fluid is ejected or aspirated plug n: a mass which is sufficiently large in cross section to fill and seal a hole chamber n: a volumetric portion of a divided barrel cock v: to take a step preparatory to actuation of a device, for example, to set or prepare a valve to open on a next step conduit sleeve n: an elongated hollow tube affixed to a stopper wherethru liquid is discharged from a chamber of a syringe conventional adj: sanctioned by general custom; i.e. commonplace, ordinary disparate n: when used to describe a first volume of contents relative to another volume of contents, the first volume of contents being kept distinctly separate from the other volume of contents differential pressure ($\Delta P$) n: a pressure gradient resulting from unequal pressures exerted upon opposing sides of a structure; generally as used herein, $\Delta P = P_p - P_d$, where subscript "p" represents proximal and subscript "d" represents distal.

distal adj: a term which depicts placement away from a reference point (e.g. away from a user of a syringe)

downstream adj: a direction which is consistent with flow out of a syringe or away from a user fluid n: a substance (e.g. a liquid or gas) which tends to take the shape of a container front adj/n: when referenced to a syringe, a distally disposed or a distally disposed site (e.g. a front of a syringe comprises the luer fitting orifice)

gas n: a fluid which is neither solid nor liquid liquid n: a fluid which is neither solid nor gaseous, free flowing like water liquid only zone n: a space within a syringe barrel which can only be physically occupied by liquid (see Thorne 862)

medial adj: occurring away from an outer edge; disposed near the center of (e.g. disposed away from an edge or periphery and in the vicinity of a center of gravity or axis of symmetry)

$P_d$ n: pressure at a site distal to a place of reference plunger rod n: a portion of a syringe piston apparatus, usually affixed to a plunger tip, to which force is applied to displace fluid within a syringe barrel plunger n: a portion of a syringe piston apparatus usually affixed to a plunger rod which is used to displace fluid within a syringe barrel prime v: to completely fill liquid into a cavity generally by removing air therefrom (e.g. priming a gas separator)

$P_p$ n: pressure at a site proximal to a place of reference proximal adj: opposite of distal (e.g. a term which depicts placement nearer to a reference point)

rear adj: opposite from front (i.e. generally associated with a part of a syringe barrel which is proximal to a syringe user relative to an outflow orifice)

reflux n: a type of retrograde (upstream) flow, usually undesired state n: a mode or condition of matter, e.g. gaseous, liquid or solid or of a device, such as an open state of a valve stiction n: a special case of friction; stiction being related to the force required to initiate motion to a resting body, esp. when that force is greater than friction associated with a moving body stop n: an obstruction which is differentiated from friction or stiction which halts displacement of a stopper or plunger stopper n: a plug substantially adv: to the most reasonable amount possible syringe n: a medical device used for injecting or withdrawing fluids upstream adj: a direction which is against the direction of flow from a syringe (opposite of downstream)

valve n: a device which has at least two stable states, in one state being closed to flow and in the other state being open to flow valve stem n: an elongated part which fits within a conduit sleeve as part of a plug or stopper and providing a part of a normally closed valve

BRIEF SUMMARY AND OBJECTS OF THE INVENTION

In brief summary, this novel invention alleviates all of the known problems related to providing a valve, according to the instant invention, which can be used to divide a barrel of a medical syringe into two adjacent chambers in which fluids are kept disparate until the valve is actuated (opened). In one embodiment, the valve is actuated by placing a predetermined pressure about the valve for the purpose of opening the valve to permit fluid flow between two chambers disposed about the valve and, thereby, permit mixing. In another embodiment, valve actuation may be in two steps thereby permitting pressure placed upon the valve to act as a cocking step, then the pressure across the valve being required to be reduced below the cocking level before valve opening. In this manner, a user is in full control of flow dispensed from a proximal chamber of an associated syringe after the valve is opened.

In brief summary, then, the instant invention is to a pressure actuated valve which can be used within a conventional syringe barrel having a hollow, elongated internal cylindrical surface which is contiguous and of substantially constant diameter to an open proximal end and to a distal end which provides a closed interior about an orifice through which fluid is transferred.

The valve has a body which when disposed within the syringe barrel is so shaped and sized to be slideably displaced along the interior surface of the barrel to function in a manner similar to a conventional syringe plunger while being so displaced. The body is generally made from two parts, each part being made from material which is substantially inert relative to fluids which reside within the syringe barrel. Generally, the body may be made from the same material used to form a plunger (e.g. one made of butyl rubber) of a plunger and rod subassembly of a conventional syringe. The parts comprise complimentary geometry which provide for joining the parts together to form a hollow chamber or cavity within the body.

Each of the joined parts comprise an elongated hollow tube, each tube having a hollow communicating pathway disposed therein. A pathway of one of the tubes is sized and shaped to be inserted into sliding but sealing engagement with the other tube to complete a closed surface within the hollow chamber thereby providing a sealed hollow chamber. The chamber is filled with compressible matter (e.g. gas or air), which after chamber sealing is confined at a predetermined pressure. The hollow pathway of the inserted tube provides a fluid communicating pathway, unless blocked by a plug or stopper, through the valve.

A plug or stopper part, sized and shaped to block the fluid communicating pathway is disposed within that pathway to provide a closed state of the valve. Displacement of the plug or stopper part out of the fluid communicating pathway opens the valve.

At least one of the joined parts comprises structure which is more pliant relative to the other part, thereby permitting compression of the chamber when pressure outside the valve exceeds pressure within the hollow chamber. For example, in the case of gas being disposed within the hollow chamber, volumetric change may be calculated using the natural gas law: (i.e. $PV=nRT$, where P is the pressure within the chamber, V is the chamber volume, n is the molecular count of gas molecules within the chamber (gas mass), R is the gas constant and T is temperature of gas within the chamber). It is readily seen that, if temperature is relatively constant, as pressure is increased, gas volume is decreased.

Because one of the parts is more pliant than the other part and the tubes are joined along a common pathway, compression of the chamber results in displacement of one tube within the other tube. The plug or stopper part is so disposed within the fluid communicating pathway that, in one embodiment of the valve, the plug or stopper is displaced from the pathway to open the valve when a pressure gradient across the valve decreases volume (compresses the valve body) within the chamber a predetermined amount. In another embodiment, displacement of one tube relative to the other tube establishes a cocking condition for plug or stopper displacement when pressure external to the valve is relieved. In this case, the plug or stopper is displaced and the valve is opened subsequent to a predetermined pressure being applied across the valve followed by relief of the applied pressure.

It may be noted that pressure within the hollow chamber decompresses the chamber once pressure external to the valve is relieved. To aid recovery of chamber size and shape following application of external pressure, the inserted tube may be frustoconicallly shaped. In this case, energy required to force the external tube about the internal tube is stored to resultantly act to force displacement of the internal tube relative to the external tube toward an initial state. It may be noted that a spring disposed to be compressed when the inserted tube is move further into the external tube may also be used to provide energy to force tube positioning toward the initial state.

If the valve is employed for a sequential delivery application, gas resident in the proximal chamber should be retained within the proximal chamber such that only liquid is delivered therefrom. For this purpose, the body may comprise another elongated tube which is disposed about the communicating fluid pathway and extends proximally into a liquid only zone (a space where only liquid can reside within the proximal chamber of a sequential delivery syringe (see Thorne 862)).

To displace the stopper upon pressure release, an elongated rod, affixed to the stopper, is extended proximally into the other elongated tube. A latching member is affixed to the rod at the proximal end thereof. As the body chamber is compressed, the latching member is displaced to latch, preferably at the proximal end of the other elongated tube. Once pressure is relieved from the valve and the chamber expands, the latched rod affixed to the plug or stopper is displaced with displacement of the other elongated tube to result in displacement of the stopper from the fluid communicating pathway. In this manner, the valve is opened upon relief of pressure disposed upon the valve rather than when pressure is applied upon the valve. Thus, pressure applied within a proximal chamber is not applied to thereby effect a high rate of dispensing fluid flow as the valve is released.

For a mixing syringe application, the distal part of the valve is constructed to be more deformable than the proximal part of the valve. For a sequential delivery syringe, the proximal part of the valve is constructed to be more deformable than the distal part. In either case, deformation of one part of the valve relative to the other part results in a linear displacement of one inserted elongated tube relative to the other associated tube. It is that displacement which acts to actuate the valve by ultimately providing for dislodging the stopper from the fluid pathway.

In the case of the mixing syringe, the stopper may be captured, upon being displaced proximally from the fluid pathway, within a cage or compartment. The cage may comprise geometry which, in cooperation with the stopper, creates a one-way valve. In this case, fluid flow can only be directed from the proximal chamber into the distal chamber, where mixing occurs. Notably, in this case, the valve may displace proximally as fluid is dispensed into the distal chamber.

In another embodiment which also uses the stopper to form a one-way valve, the stopper may be made from hydrophobic filter material through which gas readily passes, but liquid is stopped by the one-way valve. In this embodiment, liquid and gas are exchanged between the two syringe chambers. It should be noted that, even though gas may be totally discharged from the distal chamber, liquid may still be delivered into the distal chamber because successive compression of the valve results in proximal valve displacement each time pressure is reduced following a pressurized charge of liquid being delivered to the distal chamber.

In both cases, as part of delivery of diluent from the more proximal chamber into the distal chamber, the pressure actuated valve is moved distally and into contact with the more proximally disposed plunger part, thus permitting evacuation of the more proximal chamber and delivery of a dilution fluid into the distal chamber. If gas is permitted to be displaced into the more proximal chamber, provision for evacuating that gas through the rear of the syringe should be provided to dispel likelihood of delivering gas along with mixed liquid.

It may be desirable to provide a combination mixing and sequential delivery syringe for providing a flush following delivery of a mixed dose. For such a combination, a mixing syringe valve is disposed to provide separation between a distal chamber and a middle chamber and a sequential delivery valve is disposed to provide separation between the middle chamber and a proximal chamber.

The mixing syringe valve may be pressure actuated similar to the valve as disclosed for the simple mixing syringe supra. However, as is apparent to one skilled in multi-chamber syringe art, the sequential delivery valve should not be actuated by pressure (due the possibility of inadvertent activation of the sequential delivery valve when the mixing syringe valve is actuated). For this reason, a collision actuated valve, similar to the valve disclosed in Thorne 862 is employed for the sequential delivery valve.

Mixing operation of the combination mixing and sequential delivery syringe is substantially identical to mixing operation of the simple mixing syringe. It should be noted, however, that upon fully dispensing liquid from the middle chamber (the more proximal chamber in the simple mixing syringe), the mixing syringe valve and sequential delivery syringe valves are preferably driven together, thus eliminating the middle chamber.

With the two valves so joined, an element, which is associated with the mixing syringe valve, has a distal sensing end which is displaced at collision between the mixing syringe valve and distal syringe end (at the exit orifice) as the distal or mixing chamber is emptied of dispensed mixed fluid. Displacement of the distal dispensing end is communicated proximally to a valve stem of the sequentially delivery valve to actuate the sequential delivery valve once the distal chamber is emptied. Such actuation provides opportunity to deliver a liquid flush from the proximal chamber only after complete dispensing of liquid from the distal chamber.

Method for a Sequential Delivery Syringe

Use of each device employing either the sequential delivery and mixing syringe embodiments is straight forward. As an example, dispensing fluids disparately from a sequential delivery syringe involves the steps of:

disposing a sequential delivery embodiment of the valve into a conventional syringe to provide a proximal and distal chamber;

filling each proximal and distal chamber with fluid;

displacing a plunger and plunger stem assembly of the conventional syringe to displace the valve distally, thereby dispensing fluid from the distal chamber until the valve contacts the interior of the barrel which closes about the orifice;

increasing force upon the plunger stem assembly to increase pressure upon the valve and, as a result, compress the compressible portion of the valve to displace the latching part to latch at a latching site associated with the additional elongated tube which provides a pathway to the liquid only zone; and releasing force upon the plunger stem assembly permitting pressure upon the valve to decrease, thereby permitting the valve body to expand and displace the additional elongated tube proximally, thereby displacing the stopper from the common pathway and opening the valve.

Method for a Mixing Syringe

Employing the pressure actuated valve within a conventional syringe as a mixing syringe comprises the steps of:

displacing the valve into the syringe barrel to provide a proximal and a distal chamber;

providing a predetermined amount of matter for mixing in the distal chamber;

affixing a cap to close the orifice of the syringe, thereby providing a distal chamber which is closed at proximal and distal ends;

providing liquid (diluent) for mixing in the proximal chamber which remains disparate from the matter in the distal chamber until the valve is opened and closing the proximal chamber at the proximal end with a plunger and plunger stem assembly;

forcing the plunger and plunger stem of the syringe by distal displacement into the syringe to increase pressure within the syringe to the predetermined amount above the predetermined pressure to open the valve; and serially displacing the plunger and plunger stem assembly back and forth to pump liquid from the proximal chamber into the distal chamber for mixing of the matter and liquid.

Method for a Combination Mixing/Sequential Delivery Syringe

Employing a pressure actuated and syringe distal end sensing valve within a conventional syringe in substantially the same manner as for the simple mixing syringe comprising the steps of:

displacing the valve into the syringe barrel to provide a first proximal chamber and a distal chamber;

providing a predetermined amount of matter for mixing in the distal chamber;

affixing a cap to close the orifice of the syringe, thereby providing a distal chamber which is closed at proximal and distal ends;

providing liquid (diluent) for mixing in the first proximal chamber which remains disparate from the matter in the distal chamber until the valve is opened;

displacing a displacement actuated valve proximal to the first proximal chamber to provide a more proximal chamber within the syringe barrel and cause the first proximal chamber to become a middle chamber;

providing a volume of liquid, which may be used for flushing, in the more proximal chamber and inserting a plunger and plunger stem assembly into the proximal end of the syringe to enclose all chambers;

forcing the plunger and plunger stem of the syringe by distal displacement into the syringe to increase pressure within the syringe to the predetermined amount above the predetermined pressure to open the pressure actuated valve; and serially displacing the plunger and plunger stem assembly back and forth to pump liquid from the middle chamber into the distal chamber for mixing of the matter and liquid;

removing the cap, purging any gas from the distal chamber and dispensing the resultant mixture;

sensing the distal syringe end as the liquid is dispensed by displacement of a sensor which further communicates with a valve stem of the displacement actuated valve to open the displacement actuated valve upon completion of dispensing of the mixture; and dispensing solution from the more proximal chamber.

Accordingly, it is a primary object to provide a novel pressure actuated valve which in one embodiment can be employed within a conventional syringe to provide a sequential delivery syringe and in another embodiment to provide a mixing syringe.

It is another primary object to provide a pressure actuated valve which is opened by application of a pressure applied by a plunger rod assembly within the barrel of a closed syringe.

It is another primary object to provide a pressure actuated valve having a body of which a portion that is compressible.

It is an object to provide a mixing syringe from which gas is evacuated through a plunger rod assembly of the syringe such that only liquid is disposed within the syringe at the end of a mixing cycle.

It is an important object to provide a mixing syringe which is closed to communication with the exterior environment during mixing.

It is an important object to provide a sequential dispensing syringe which is closed to a more proximal chamber during filling of the distal chamber.

It is a fundamental object to provide a combination mixing and flushing syringe having a pressure actuated valve and a displacement actuated valve which provide predetermined control for displacing fluid from each of three chambers of a conventional syringe, each valve being selectively actuated for, first, mixing of matter and diluent from a middle chamber into a most distal chamber, then, second, sequential delivery of liquid from a most proximal chamber.

These and other objects and features of the present invention will be apparent from the detailed description taken with reference to accompanying drawings.

BRIEF DESCRIPTION OF THE DRAWINGS

FIG. 5 is a perspective of the pressure actuated valve seen in FIG. 1.

FIG. 6 is a cross section of the pressure actuated valve seen in FIG. 5.

FIG. 7 is an exploded cross section of an embodiment of the valve seen in FIG. 5.

FIG. 8 is a cross section of the valve seen FIG. 6 compressed by applied external pressure.

FIG. 9 is a cross section of the valve seen in FIG. 6 with a stopper removed from a medially disposed fluid flow pathway to yield an open state of the valve.

FIG. 10 is a cross section of an embodiment of the valve seen in FIG. 6 wherein a stopper displaced from the medially disposed fluid flow pathway is captured in a compartment formed to provide a one way valve.

FIG. 11 is a contour map of an exit orifice from which the stopper is displaced to open the valve as seen in FIGS. 9 and 10.

FIG. 12 is a cross section of the valve seen in FIG. 6, but without a stopper capturing cavity.

FIG. 13 is a cross section of a distal part of the exploded view of FIG. 7 magnified to show detail of raised rings about an elongated medial tube.

FIG. 16 is a cross section of a plunger of a plunger and rod assembly, the plunger incorporating a gas only communicating one-way valve whereby gas may be dispensed from the proximal chamber of the syringe.

FIG. 24 is a perspective, of the pressure actuated valve seen in FIG. 16, permitting a portion of the distal side of the valve to be viewed.

FIG. 25 is a perspective, of the pressure actuated valve seen in FIG. 16, permitting a portion of the proximal side of the valve to be viewed.

FIG. 26 is a cross section of the pressure actuated valve seen in FIGS. 24 and 25.

FIG. 26A is an exploded view in cross section of the pressure actuated valve seen in FIG. 16.

FIG. 26B is a cross section of a stopper which is rotated 90° when compared to the same part seen in FIG. 26A and displaced to open the valve.

FIG. 27 is a cross section of a compressed valve with the stopper in cocked state preparatory to being displaced from obstructing a medially disposed flow path of the valve.

FIG. 28 is a cross section of a decompressed valve with the stopper displaced from the flow path to open the valve.

FIG. 30 is a perspective of a conventional syringe divided into three chambers by a distally disposed pressure actuated valve, a medially disposed displacement actuated valve and a proximally disposed syringe plunger.

FIG. 31 is a perspective similar to the perspective seen in FIG. 30 with the pressure actuated valve displaced proximally into direct communication with the displacement actuated valve thereby reducing the number of chambers within the syringe to two.

FIG. 32 is a perspective similar to the perspective seen in FIG. 31 wherein the distal chamber has been emptied and fluid in the proximal chamber is being dispensed.

FIG. 39 is a cross-section of a plunger portion of the displacement actuated valve seen in FIG. 30.

FIG. 40 is a side elevation of a plunger stem portion of the displacement actuated valve seen in FIG. 30.

FIG. 41 is a cross-section of an assembled displacement actuated valve seen in FIGS. 39 and 40.

FIG. 42 is a magnified cross-section of communicating pressure actuated and displacement actuated valves as seen in FIG. 31.

FIG. 43 is a magnified cross-section of communicating pressure actuated and displacement actuated valves as seen in FIG. 32 (with the syringe end sensor and plunger stem displaced to open the displacement actuated valve).

DETAILED DESCRIPTION OF THE ILLUSTRATED EMBODIMENTS

Reference is now made to the embodiments illustrated in FIGS. 1-43 wherein like numerals are used to designate like parts throughout. Primes of numbers are used to indicate an item which is like another item so numbered but having one or more elements of differentiation.

Mixing Syringe Embodiment

Figure 1:
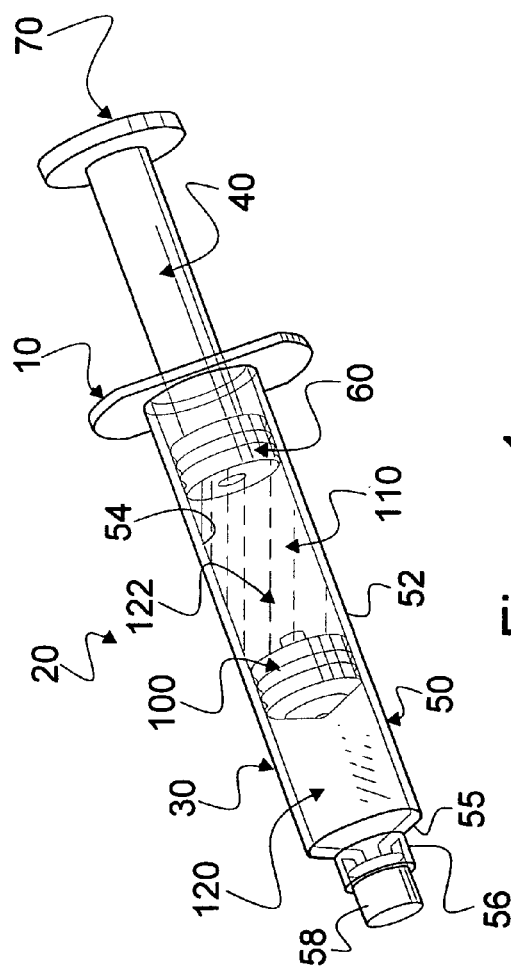
FIG. 1 is a perspective of a conventional medical syringe with plunger and rod subassembly and with a pressure actuated valve disposed within the barrel of the syringe to divide space within the barrel into a distal and a proximal chamber and thereby provide for a mixing syringe.

Reference is now made to FIGS. 1-16 wherein mixing syringe embodiments are seen. Using a pressure actuated valve, a conventional syringe 10 may be employed in construction of a mixing syringe 20, as seen in FIG. 1. Syringe 10 is generally provided with a barrel part 30 and a plunger and rod assembly 40. Barrel part 30 comprises a barrel 50 which is an elongated hollow tube 52 with a smooth, circular inner surface 54 which is substantially of constant diameter and obstructed at a distal end 55 at a luer fitting 56 by a cap 58.

Plunger and rod assembly 40 is usually constructed with two parts, a plunger 60 and an elongated rod 70 by which plunger 60 is displaced within syringe barrel 50. Plunger 60 is sized and shaped to wipe matter from surface 54 and to displace fluids disposed within barrel 50.

For a mixing syringe embodiment of the instant invention, a pressure actuated valve 100 is initially disposed within barrel 50 to separate barrel space into two chambers, i.e. proximal chamber 110 and distal chamber 120. As seen in FIG. 1, commonly a liquid diluent 122 is disposed in proximal chamber 110.

Valve 100 is seen in FIG. 5 to comprise a cylindrical grooved side surface 124 which is sized and shaped to act as a plunger which wipes interior surface 54 while being displaced within barrel 50. Further valve 100 comprises a distal face 126 which is sized and shaped to nest with distal end 55 of syringe barrel 50 and a proximal face 128 which comprises a compartment 130 about a medially disposed pathway, not seen in FIG. 5. Generally, valve 100 is made by assembly of two plunger parts, a distal part 140 and a proximal part 150.

Construction of valve 100 is better seen in FIG. 6. Proximal part 150 part is seen to comprise surface 124, compartment 130 and proximal face 128. Internally, part 150 comprises a hollow cylindrical surface section 152, better seen in FIG. 7. Surface section 152 is interrupted by an annular groove 154, proximally disposed relative to a circular opening 156. Medially disposed within part 150 is a hollow elongated tube 160 which communicates with an internal portion 162 of compartment 130. Further, tube 160 comprises a hollow pathway 164 which forms a pathway for fluids 165, when unblocked.

As seen in FIGS. 6 and 7, distal part 140 is sized and shaped to be tightly fitted into circular opening 156 and groove 154. For this purpose, distal part 140 has a locking ring 166 which extends proximally from a hollow cylindrical portion 168 for engagement in groove 154, see FIG. 6. Distal part 140 also comprises a thin distal wall 170 which communicates medially with an elongated hollow tube 172. Tube 172 is sized and shaped to sealingly slide within a portion of pathway 164. A distal portion 174 of tube 172 forms a continuation for fluid pathway 164.

A plug or stopper 180 which may be formed as a sphere or ellipsoid and sized to obstruct pathway 164 proximally is disposed to close valve 100 as seen in FIG. 6. By displacing tube 172 proximally within tube pathway 164 (within tube 160) stopper 180 is ejected from pathway 164 as seen in FIG. 8. Such ejection is accomplished by placing a pressure about valve 100 which, resultingly, acts to compress thin wall 170 more than other external parts of valve 100 because wall 170 is the most deformable part in valve 100. Thus, the internal volume 176 of valve 100 is reduced, thrusting wall 170 and tube 172 proximally inward causing stopper 180 displacement from pathway 164. Such compressive action is simply a consequence of pressure/volume relationship of the natural gas law. As an example, doubling the external pressure about valve 100 can approximately reduce compressible volume of the sealed hollow of valve 100 by a factor of approximately two. Relative displacement of tube 172 is determined by geometry of construction of compressible portions of valve 100. As an example, a wall thickness of 0.040 inches of wall 170 compared to a thickness of approximately 0.150 inches of surrounding valve 100 wall structure assures a desired compressive response.

An embodiment of an elongated hollow tube 172' which may be optionally used with distal part 140 is seen in FIG. 13. Note that tube 172' has a frustoconically shaped exterior surface 182 and a plurality of rings, generally numbered 184, which provide for sealing inside tube 160 as tube 172 is displaced proximally within tube 160. The frustoconical shape of tube 172 causes tube 160 to be elastically enlarged upon increased distance of displacement of tube 172 into tube 160. Also, optionally a spring 186, seen in FIG. 7, may be disposed about tube 172 to engage tube 160 to be compressed as face 170 is displaced and further act to force valve 100 to resume its initial geometric form when external pressure is removed. Employment of such items as the frustoconical shape and rings of tube 172' and spring 186 are not necessary unless stiction (static friction) are too great to permit valve 100 to regain an initial geometric form upon pressure reduction, as seen in FIG. 9. As is well known in the medical syringe art, increased force to displace interfacing items in a syringe due to friction (and stiction) can be reduced by treating interfacing surfaces with silicone.

To assure dispensing flow from a proximal chamber 110 into a distal chamber 120 (see FIG. 1) when valve 100 is opened by ejection of stopper 180 into compartment 130 (see FIG. 9), a distal inner surface portion 190 of compartment 130 is configured as seen in FIG. 11. As seen in FIG. 11, portion 190 has a plurality of ridges 192 and grooves 194, the ridges 192 providing a barrier against distal displacement of stopper 180 and the grooves 194 providing communicating pathways for fluid flow with pathway 164.

Stopper 180 and a compartment 130' of a valve 100' of a part 150" (similar to part 150') may be used in the formation of a one-way valve, as seen in FIG. 10. Interior geometry 196 of compartment 130' of part 150" is narrowed to conform to the diameter of stopper 180 such that fluid dispensed distally freely flows through pathway 164, but fluid drawn proximally is blocked. Note that, if stopper 180 is made of a hydrophillic material which permits passing of gas there through, but which is not permeable to liquid, the resulting valve is one-way to liquids but not to gases.

Another embodiment of a mixing syringe valve 100" is seen in FIG. 12. Note that valve 100" is differentiated from valves 100 and 100' as no compartment 130 is provided to capture stopper 180. In such a case, stopper 180 is left to freely fall into chamber 110 and is not effective in further action of valve 100".

Figure 2:
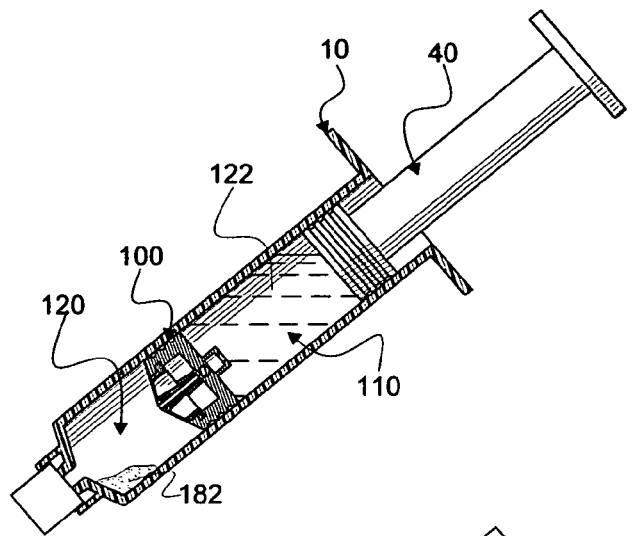
FIG. 2 is a cross section of the medical syringe seen in FIG. 1 with liquid disposed in the proximal chamber.
Figure 3:
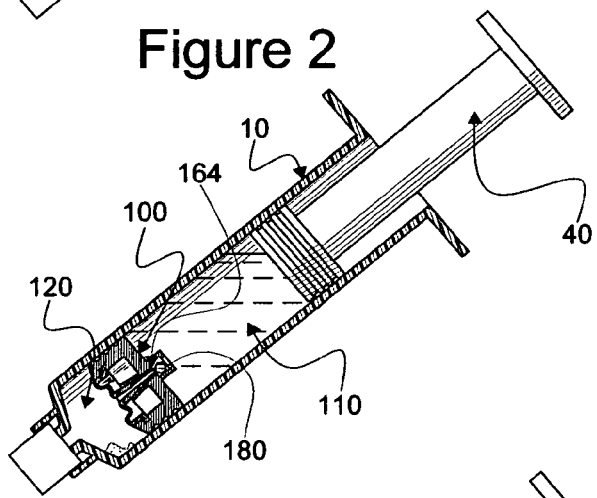
FIG. 3 is a cross section of the medical syringe seen in FIGS. 1 and 2 with the plunger and rod subassembly forced distally into the syringe to apply compressive pressure about the pressure actuated valve.
Figure 4:
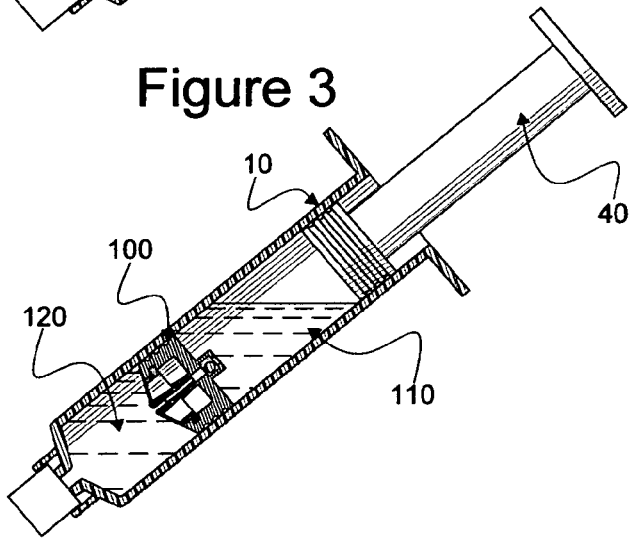
FIG. 4 is a cross section of the medical syringe seen in FIGS. 1-3 with the pressure actuated valve opened permitting liquid to be dispensed into the distal chamber and gas from the distal chamber communicated into the proximal chamber.

Reference is now made to FIGS. 2-4 wherein an exemplary method of use is seen. In FIG. 2, a mixing syringe 20 is seen to have a diluent which is disposed in proximal chamber 110. As an example a lyophilized material 182 desired to be reconstituted or a concentrate may be disposed in distal chamber 120. Note that the distal end of syringe 10 is fitted with a cap 58 such that, with plunger 60 a closed system is formed. To actuate valve 100, Plunger and rod assembly 40 is advanced distally as seen in FIG. 3. Distal advancement of plunger and rod assembly 40 increases pressure across valve 100 until distal face 170 is compressed to discharge stopper 180 from pathway 164.

Figure 15:
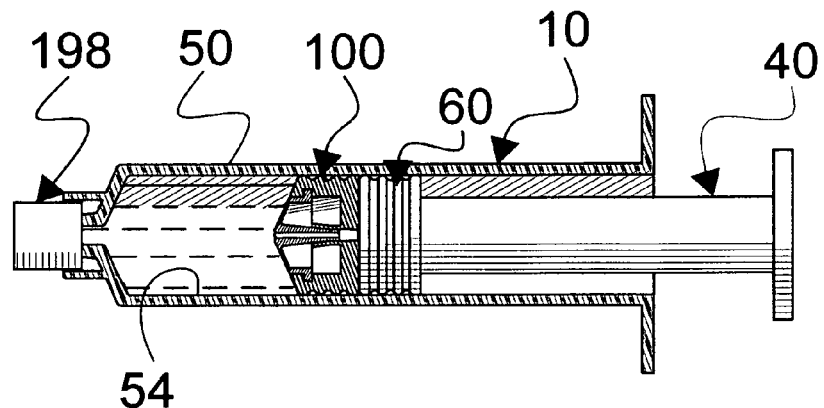
FIG. 15 is a cross section of an embodiment of a mixing syringe similar to FIG. 2, but wherein liquid has been communicated from the proximal chamber into the distal chamber and gas has been dispensed from the syringe permitting the plunger and rod assembly to engage a proximal side of the valve.

Once opened, valve 100 is permissive to fluid flow from proximal chamber 110 into distal chamber 120. Note that successively applying pressure across valve 100 results in compression of face 170. Release of the successively applied pressure and subsequent restoration of valve 100 to an uncompressed state causes face 170 to expand against any matter disposed in distal chamber 120, thereby causing valve 100 to be displaced proximally by successively applying and releasing pressure via plunger and rod assembly 40 as seen in FIG. 4. As seen in FIG. 15, if plunger 60 is provided with a hollow cavity which is sufficiently large to accept compartment 130, valve 100 may be displaced proximally to nest with plunger 60.

Figure 14:
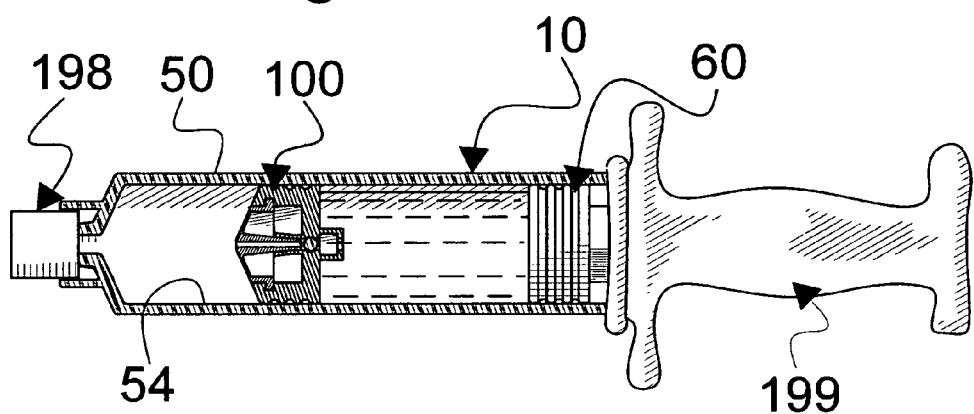
FIG. 14 is a cross section of a mixing syringe, similar to the syringe seen in FIG. 2, with a shield disposed about the plunger and rod subassembly to provide against cross contamination.
Figure 29:
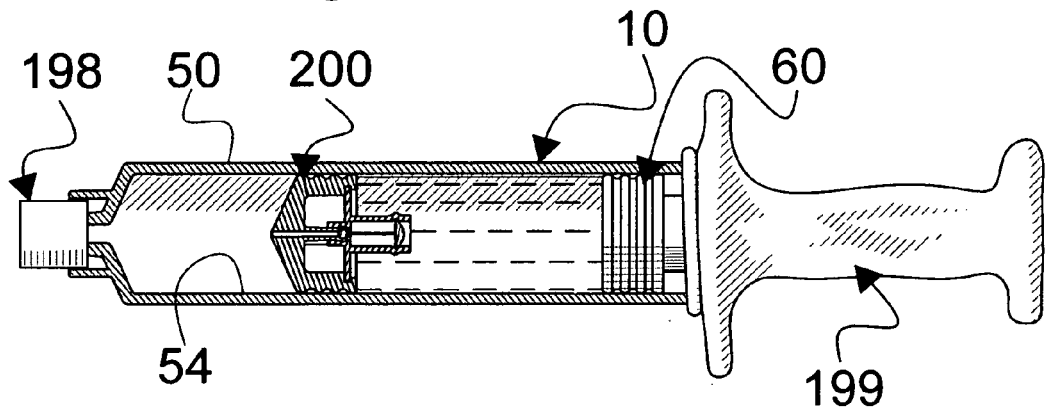
FIG. 29 is a cross section of the sequentially delivery syringe seen in FIG. 17 with a shield disposed about the plunger and rod subassembly to provide against cross contamination.

Also, as seen in FIG. 14, a shroud 199 (as disclosed in the Thorne Application, from which this U.S. Patent Application continues-in-part) may be affixed about plunger and rod assembly and a communicating portion of syringe 10 to reduce likelihood of cross contamination across the interior surface 54 of barrel 50 as plunger assembly 40 is pumped back and forth. So affixed, shroud 199 permits plunger and rod assembly to be displaced proximally and distally without concern for such cross contamination.

Sequential Delivery Syringe Embodiment

Figure 17:
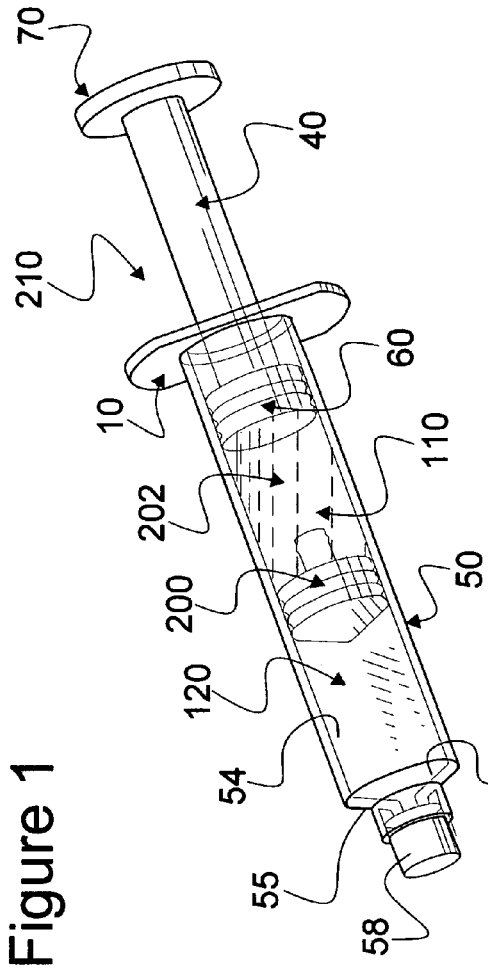
FIG. 17 is a perspective of a conventional medical syringe with plunger and rod subassembly and with a pressure actuated valve disposed within the barrel of the syringe to divide space within the barrel into a distal and a proximal chamber and thereby provide for a sequential delivery syringe.

Reference is now made to FIG. 17 wherein a pressure actuated valve 200, made according the present invention, is seen disposed for use in a sequential delivery syringe 210. Similar to valve 100, a valve 200 divides barrel 50 into two disparate chambers, a proximal chamber 110 and a distal chamber 120. However, rather than mixing two reagents in distal chamber 120, any reagent in chamber 120 is fully emptied before dispensing of fluid from proximal chamber 110. It is very important that valve 200 not open until all of fluid initially contained within chamber 120 is dispensed. It is also important that distal chamber 120 be filled and emptied in the same manner as a single chamber conventional syringe is filled and emptied.

Another important consideration for a sequential delivery syringe is that it is important that dispensing of fluid from the proximal chamber 110 is under control of a user. In other words, it is important that a positive pressure required to switch valve 200 not be applied at the time of valve switching to thereby uncontrollably accelerate fluid resultantly dispensed from proximal chamber 110.

For a sequential delivery syringe embodiment of the instant invention, pressure actuated valve 200 is initially disposed within barrel 50 to separate barrel space into the two chambers, proximal chamber 110 and distal chamber 120. As seen in FIG. 17, commonly a flush liquid 202 is disposed in proximal chamber 110.

Valve 200 is seen in FIGS. 24 and 25 to comprise a cylindrical grooved side surface 124' which is sized and shaped to act as a plunger which wipes interior surface 54 while being displaced within barrel 50 (see FIG. 17). Further, valve 200 comprises a distal face 126' which is sized and shaped to nest with distal end 55 of syringe barrel 50 and a proximal face 128' which has an elongated hollow tube 211 to define a medially disposed pathway, not seen in FIGS. 24 and 25. Generally, valve 200 is made by assembly of two plunger parts, distal part 140' and proximal part 150' (see FIGS. 26-8).

Construction parts of valve 200 are seen in exploded format in FIG. 26A. Proximal part 150' is seen to comprise a proximally disposed elongated hollow tube 211 and a distal elongated hollow tube 220. Hollow portions of tubes 211 and 220 communicated to form an open pathway 230. Tube 211 ends proximally at edge 212. A disk shaped section 238 extends orthogonally from tube 211.

A distal part 140' comprises a distal face 240 which is sized and shaped to conform to internal surface 242 of end 55 of barrel 50. Further, part 140' has an integral, medially disposed hollow tube 250 defining a continuous through-hole pathway 252. Disposed within a medial core of part 140' is a hollow compartment 254. Compartment 254 is characterized by a proximally disposed annular groove 256. Groove 256 is sized and shaped to accept disk 238 and form a seal there between. Likewise, tube 250 is sized and shaped to fit sufficiently tightly within tube 220 to form a sliding seal such that tube 250 may be displaced along pathway 230 while maintaining the seal. Note that pathway 252 communicates with pathway 230 when parts 140' and 150' are joined.

A stopper part 260 comprises a plug 262, and an elongated stem 264 and a cap or flange portion 266. Plug 262 may be ball or spheroidally shaped. Stem 264 is long and narrow but strong enough not to break as plug 262 is displaced. Flange portion 266 is a flattened part which extends laterally along a first axis as seen in FIG. 26A, but is thinned along a second axis (orthogonal to the first axis) as seen in FIG. 26B. Thinned parts 264 and 266 as so sized to permit fluid flow through pathway 230.

Parts 140' and 150', like parts 140 and 150, are made from material commonly used in manufacture of syringe plungers. A common material for such use is butyl rubber, a material which is incompressible, yet elastic and deformable.

Valve 200 is seen assembled in FIG. 26. When so assembled, a chamber 176' (formed by assembly of parts 140' and 150'), is sealed and substantially gas tight. Plug 262 is disposed within pathway 280 to close valve 200. Stem 264 also resides in pathway 230, but flange 266 does not extend proximally to edge 212. Since material of part 150' is deformable, flange 266 simply deforms tube 211 and pathway 230. Similarly, plug 262 deforms tube 220 to form a tightly sealed closure of pathway 230.

Opening of valve 200 is accomplished as seen in FIGS. 27 and 28. As a first opening stage, sufficient external pressure is applied upon valve 200 to collapse disk 238 inward. As is well known, the natural gas law states $PV=nRT$, where P is pressure, V is an enclosed volume, n is the number of particles (molecules) within the enclosed volume, R is a gas constant for gas contained within the volume and T is temperature of gas within the volume. Thus an application of increasing external pressure yields a pressure differential which causes a yieldable part (in this case disk 238) to be displaced inwardly, as seen in FIG. 27. Applying sufficient external pressure, causes disk 238 to yield to displace flange 266 to be in contact with edge 212, forming a latch. Note at this moment, valve 200 remains closed. Plug 262 still closes pathway 230. It should also be noted that inadvertent switching of valve 200 is readily resolved by requiring a significant pressure above pressure generated within barrel 50 of syringe 210

As an example, a conventional 20 ml syringe requires about 0.5 pounds of pressure applied by force on a plunger stem to displace a plunger. An external force of ten or more pounds may be designed into valve 200 to cause flange 266 to be displaced into contact with edge 212, making inadvertent valve 200 opening extremely unlikely.

Opening of valve 200 occurs in a second step, as seen in FIG. 28. When external pressure placed upon valve 200 is relieved, pressure within chamber 176' forces disk 238 to an initial, uncollapsed state which displaces plug 262 from pathway 230, opening valve 200. In this manner, pressure applied to open is relieved before valve 200 opens thus reducing uncontrolled fluid flow upon valve 200 opening.

Figure 18:
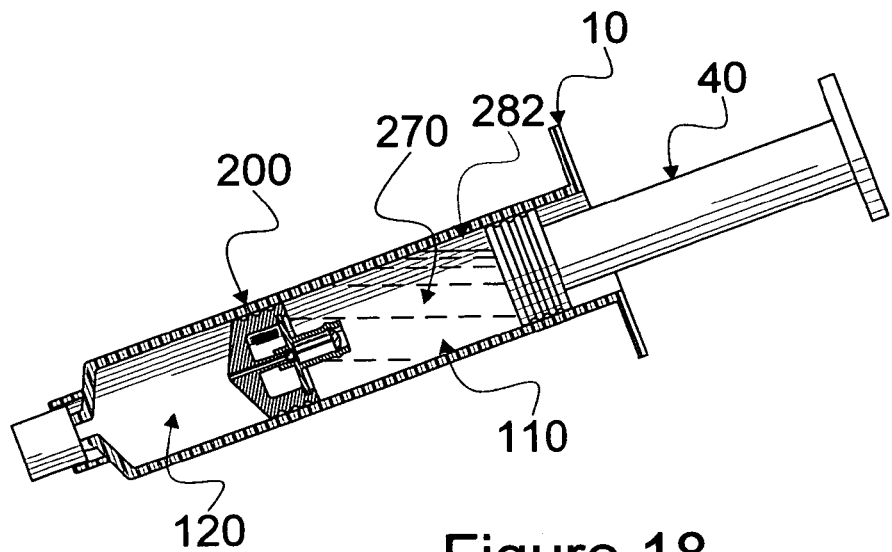
FIG. 18 is a cross section of the medical syringe seen in FIG. 1 with liquid disposed in the proximal chamber.

Reference is now made to FIGS. 18-23, wherein steps for a method of use of valve 200 in a sequential delivery syringe are seen. In FIG. 18, a syringe 10 having a valve 200 disposed within barrel 50 to provide a proximal chamber 110 and a distal chamber 120. A volume of liquid 270 (usually for flushing) is disposed in chamber 110. Also, a small volume of gas 282 (e.g. air) is also resident in chamber 110 as a natural result of filling and/or out gassing.

Figure 19:
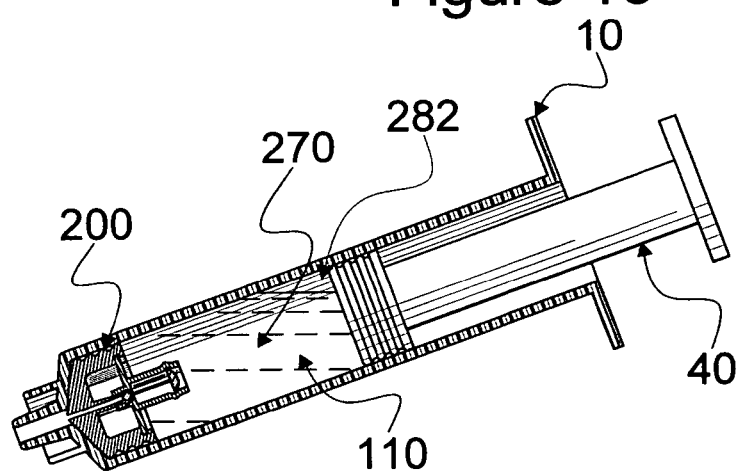
FIG. 19 is a cross section of the medical syringe seen in FIGS. 17 and 18 with the plunger and rod subassembly forced deeply into the syringe such that the distal chamber is emptied.
Figure 20:
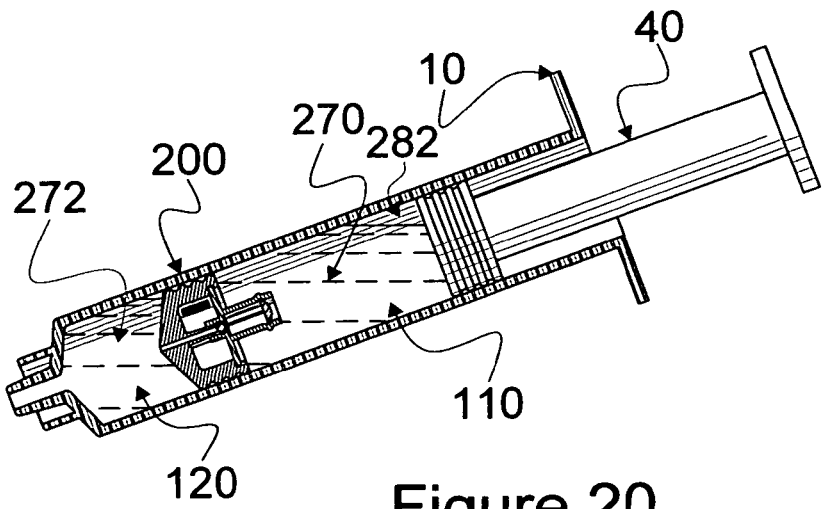
FIG. 20 is a cross section of the medical syringe seen in FIG. 19 with liquid drawn into the distal chamber.

Syringe 10 may be used to draw in a sample of liquid 272 into chamber 120 as seen in FIGS. 19 and 20. As seen in FIG. 19, plunger and rod assembly 40 is displaced distally until chamber 120 is emptied. Then syringe 10 is disposed to draw desired liquid 272 into chamber 120 as seen in FIG. 20. Note that valve 200 remains closed through steps of FIGS. 19 and 20 because force upon plunger and rod assembly 40 is only sufficient to displace valve 200 within barrel 50.

Figure 21:
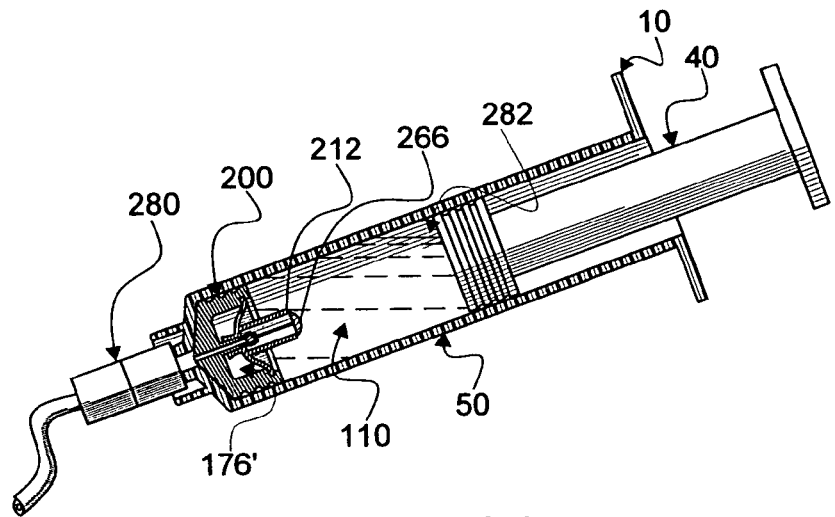
FIG. 21 is a cross section of the medical syringe seen in FIG. 20 with liquid fully dispensed from the distal chamber and compressive force applied to the pressure actuated valve.
Figure 22:
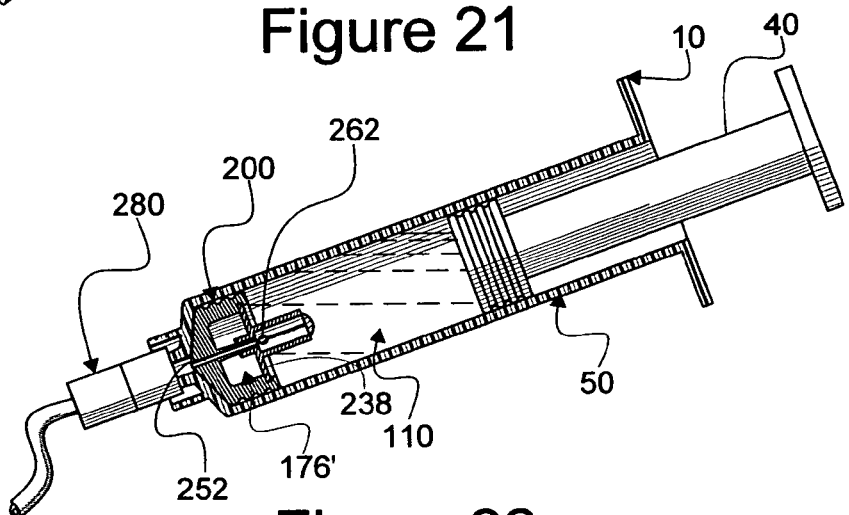
FIG. 22 is a cross section of the medical syringe seen in FIG. 21 with pressure upon the valve relieved by proximal displacement of the plunger and rod assembly, relief of pressure displacing a stopper from a fluid flow pathway to open the valve.
Figure 23:
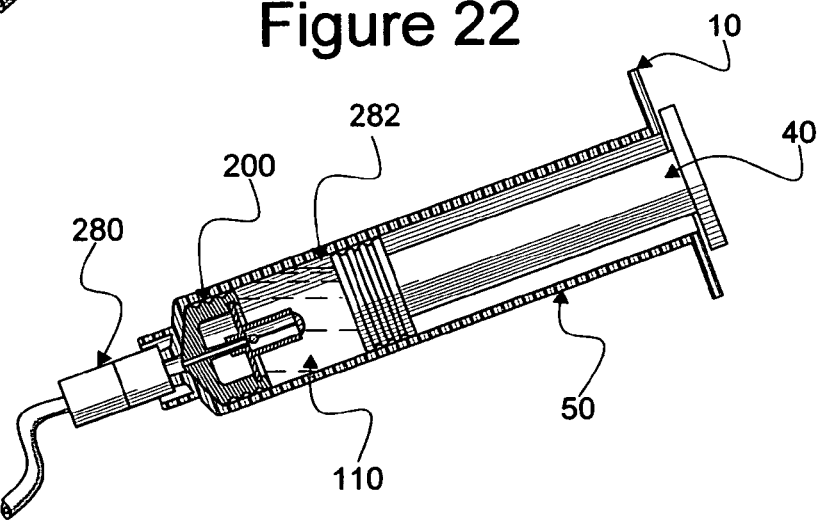
FIG. 23 is a cross section of the medical syringe seen in FIG. 22 with liquid partially dispensed from the proximal chamber.
Figure 34:
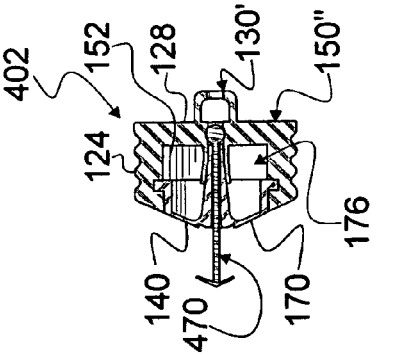
FIG. 34 is a cross-section of the valve seen in FIG. 33.
Figure 35:
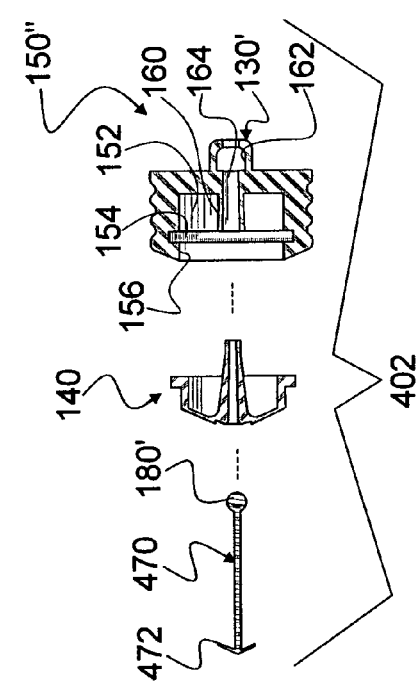
FIG. 35 is an exploded cross-sectional view of the valve seen in FIG. 34.

After the bolus of fluid 272 first to be dispensed is resident in chamber 120 (see FIG. 20), a fluid dispensing connection 280 is affixed to syringe 10 (see FIGS. 21-23). Fluid 272 drawn into chamber 120 is seen to be fully dispensed, after which, increased force upon plunger and rod assembly 40 to collapse valve 200 to displace flange 266 into contact with edge 221 is seen in FIG. 21.

As seen in FIG. 22, pressure upon plunger and rod assembly 40 is relieved, pressure inside chamber 176' of valve 200 restores initial geometry of chamber 176' and disk 238 to an initial state thereby displacing plug 262 from pathway 252 to open valve 200. A major portion of the liquid 270 resident in chamber 110 is then dispensed as seen in FIG. 23. Note, that air 282 is not available within the liquid only zone and is therefor retained in chamber 110, which is not totally emptied.

Noting that plunger and rod assembly 40 is displaced bidirectionally within barrel 50 in steps seen in FIGS. 18-23 and to minimize likelihood of cross contamination by such displacement, it is recommended that a shield 199 be affixed about syringe 10 as seen in FIG. 14. Shield 199 is disclosed in more detail in the Thorne Application.

Air may be selectively discharged through a plunger of a plunger and discharge assembly to eliminate concern for dispensing air from chamber 110. A plunger 300 through which such discharge may be accomplished is seen in FIG. 16. As seen in FIG. 16, plunger 300 is externally configured like a conventional syringe plunger about exterior side 310. Medially and distally disposed is an entry hole 320. Hole 320 is sized and shaped to enclose sealingly about a hydrophobic filter 330 made of a material selected to pass gas, but be impervious to liquids. Such filter material is well known commercially today. Hole 320 is closed proximally by a thin membrane 340 molded as a part of plunger 300. Medially disposed across membrane 340 is a slit 350 which forms a one-way valve, permitting air to be discharged proximally under pressure of a distally forced 70 rod, but not permissive to air being displaced distally to re-enter syringe 10. In this manner, by holding syringe 10 vertically upright with plunger and rod assembly 40 held in a superior position, and forcing plunger 70 downward, gas is caused to flow out of syringe 10. In this manner gas may be eliminated from chamber 110 in either a mixing syringe or sequentially delivery syringe embodiment.

Combination Mixing/Sequential Delivery Syringe Embodiment

It is highly desirable to provide a combination mixing and sequential delivery syringe within a single conventional syringe barrel. Reference is now made to FIGS. 30-43, and particularly to FIG. 30, wherein an exemplary embodiment of a mixing/sequential delivery syringe (otherwise referenced as a mixing/flush syringe) 400 made according to the present invention is disclosed. A conventional syringe 10 wherein a pressure actuated valve 402 is disposed to provide proximal closure for a distal chamber 120' within barrel 50. Proximally disposed relative to valve 402 a displacement actuated valve 410 provides proximal closure for a medially disposed chamber 420 within barrel 50. A plunger 60 provides closure for a more proximal chamber 430.

For use, chamber 120' is commonly filled with matter to which a diluent is added to reconstitute a drug. However, a liquid concentrate may also be in chamber 120'. Chamber 420 is most commonly filled with diluent or reconstitution liquid. Chamber 430 is generally provided with a flush solution. As chamber 430 may also contain gas which results from filling or outgassing and should no pathway for elimination of such gas be available within syringe 400, valve 410 must assure no gas is delivered from chamber 430.

As disclosed for valve 100 supra, valve 410 is actuated to an open state by applying a predetermined pressure about valve 410 via syringe plunger rod assembly 40. Successive "pumping" of assembly 40 in directions illustrated by double arrow 440 (see FIG. 31) displaces diluent, originally disposed in chamber 420, into chamber 120', thereby emptying chamber 420. Once chamber 420 empties valve 402 communicates directly with valve 410 as seen in FIG. 31.

Because valve 410 is not open when valve 402 is displaced into contact therewith, the number of effective chambers becomes two, i.e. chamber 120' and chamber 430. After thorough mixing the mixture in chamber 120' is ready for delivery. With cap 58 removed and a connecting line 280 is affixed to syringe 400 (see FIG. 32), plunger and rod assembly 40 is displaced in direction of arrow 460.

When valve 402 makes contact with syringe barrel end 55, valve 410 is opened, as disclosed in detail hereafter, for delivery of fluid from chamber 430. As disclosed for valve 200, air 282 resident in chamber 430 is retained therein by evacuating only liquid from a liquid only zone.

Figure 33:
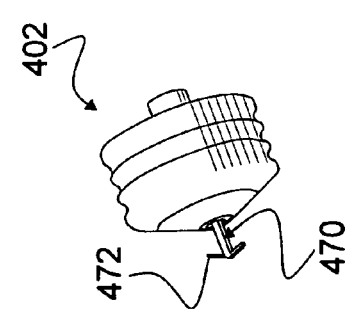
FIG. 33 is a perspective of a pressure actuated valve with a distally disposed syringe end sensor extending distally therefrom.
Figure 36:
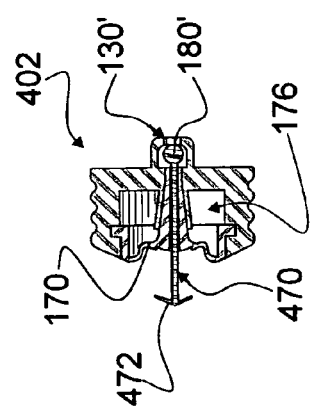
FIG. 36 is a cross-section of the valve seen in FIG. 34 whereupon a predetermined pressure gradient is imposed exterior to the valve causing a portion of the valve to compress inwardly.

Attention is now drawn to FIGS. 33-38 wherein structure and operation of valve 402 are disclosed. As seen in FIG. 33, valve 402 is a pressure actuated valve similar in form and function to valve 100'. However, valve 402 has an elongated stem 470 with a syringe barrel sensing feature 472 extending medially therefrom. As seen in cross section in FIG. 34, valve 402 comprises two plunger parts, part 140 (see also FIG. 13) and 150" (see also FIG. 10) which fit together to provide a hollow, closed internal volume 176. A distal or frontal wall 170 of valve 402 is dimensioned to be thin to constrict under externally applied pressure as previously disclosed for valves 100, 100' and 100". Under a predetermined external pressure higher than pressure within volume 176, frontal wall 170 is displaced inwardly as seen in FIG. 36 to subsequently displace stopper 180' of stem 470 proximally into compartment 130'.

Figure 37:
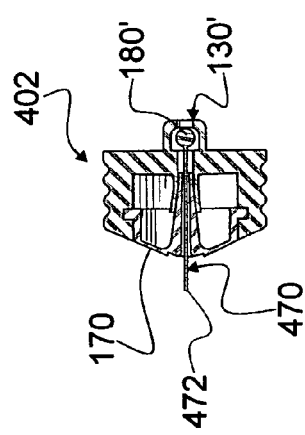
FIG. 37 is a cross section of the valve seen in FIG. 34 with the syringe end sensor rotated 90° and displaced proximally to open the valve.

Once exterior pressure is relieved, wall 170 and valve 402 are restored to an initial state as seen in FIG. 37. Note that stopper 180' remains trapped in compartment 130'. Also note that stem 470 is rotated 90 degrees in FIG. 37 to visually demonstrate planarity of sensing feature 472.

Figure 38:
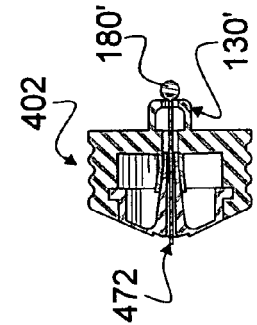
FIG. 38 is a cross section of the valve seen in FIG. 37 with the syringe end sensor further displaced proximally.

Further when sensing feature 472 contacts a barrel end 55 (see FIG. 32), stopper 180' is further displaced proximally as seen in FIG. 38. Result of such displacement is disclosed in detail hereafter.

Valve 410 which is initially disposed between diluent chamber 420 and flush solution chamber 430, as seen in FIG. 30, is also seen in cross section in FIG. 41. Valve 410 is composed of two parts, a body part 500 and a sensing plug or stopper part 510. As seen in FIG. 39, body part 500 has an exterior side wall 512 which is sized and shaped to perform as a plunger part within barrel 50. Part 500 has a medial distal cavity 514 which is sized and shaped to accept compartment 130' as seen in FIG. 42. Proximally disposed is an elongated hollow tube 211, the purpose for which is to provide access 516 to a liquid only zone, as disclosed supra. Between tube 211 and cavity 514 is a hollow cylindrical hole 518 which completes a fluid passageway 520. Cavity 514, hole 518 and access 516 combine to provide an openable passageway for liquid flow downstream from chamber 430 when valve 410 is opened.

Stopper or plug displace-able sensing part 510 is seen in FIG. 40. Part 510 comprises displacement sensing legs 522 and 524 and a bulbous plug 526. As seen FIG. 41, plug 526 initially resides within hole 518 to close valve 410.

When valve 402 is displaced proximally to contact valve 410, as seen in FIG. 42, plug 526 is not displaced. Displacement of part 510 only occurs when sensing end 472 of stem 470 contacts barrel end 55 driving stopper 180' proximally out of compartment 130' to collide with at least one sensing leg 522 or 524. Such displaces plug 526 from hole 518 to open valve 410 for delivery of flush solution.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A fluid pressure actuated valve for use in a conventional medical syringe comprising a barrel having a hollow, elongated internal cylindrical surface which is contiguous to an open proximal end and to a distal end having a closed interior about an orifice through which fluid is transferred, said valve comprising:

a body for disposal within the barrel for dividing the barrel into a proximally disposed chamber wherein a diluent can be disposed and a distally disposed chamber wherein a drug to be mixed can be disposed, said body being cylindrically shaped and sized to be slideably displaced along the surface and function as syringe plunger while being so displaced;

said body being made from two separate parts, each part being made from syringe plunger material which is incompressible, pliant and elastic, each of said parts comprising complimentary geometry by which the two parts are joined and sealed together to become a single unit comprising a common external surface which encloses a hollow internal cavity;

each of said two separate body parts further comprising a medially disposed elongated hollow tube, which comprises a hollow communicating pathway, a pathway of one tube being sized and shaped to be to be inserted to sealingly and slideably engage the other tube, thereby forming an internal closed surface for said sealed hollow cavity, said cavity being filled with compressible matter disposed at a predetermined pressure when the two parts and associated tubes are joined and to also thereby provide a common pathway for fluid flow through the valve;

a displaceable stopper comprising a bulging part sized and shaped to occlude said pathway which, in a first valve-closed-state is disposed to occlude the common pathway and in a second valve-open-state is displaced from the pathway to permit fluid flow there through; and said body further comprising distal and proximal faces which interface with the distal and proximal chambers, respectively, said faces comprising thinned portions collectively providing distortable structure about said hollow cavity such that fluid pressure within said chambers at a predetermined amount greater than the predetermined pressure effects distortion of said proximal face of said body and concurrent displacement of said bulging part of said stopper part which is displaced from said pathway causing the valve to transition from the first valve-closed-state to the second valve open state permitting fluid flow through the valve.

2. A pressure actuated valve according to claim 1 wherein said inserted tube comprises a frustoconical outer surface which stretches the receivingly engaged tube to provide a restoring force following reduction of the exterior pressure.

3. A pressure actuated valve according to claim 1, wherein one of said parts which is more proximally disposed relative to the open proximal end of the syringe as compared to the other part further comprises an additional elongated tube extending proximally to an open end which thereby communicates between the common pathway and a liquid only zone whereby only liquid is dispensed from the proximal chamber.

4. The pressure actuated valve according to claim 3 wherein said stopper further comprises a rod comprising a length which extends proximally to a latching part which is sized for disposal within said additional elongated tube when the valve body is undistorted and said stopper is in the first valve-closed-state but which has latching geometry such that, when a predetermined external pressure is applied to distort said body, the latching part is delivered beyond the open end of the additional elongated tube whereat, prior to the body becoming undistorted, the stopper remains latched and then after the body becomes undistorted the stopper is displaced by action of the additional tube upon the rod and latching part to pull the stopper free and switch the valve to the second valve-open-state, thereby permitting displacement of the stopper upon reduction of distorting external pressure and reducing likelihood of inadvertent uncontrolled fluid flow when the valve is opened.

5. The pressure actuated valve according to claim 4 wherein said proximal part is more easily deformable than said distal part.

6. A method for using a pressure actuated valve to divide a conventional medical syringe into two chambers to dispense disparate fluids from each chamber sequentially, said method comprising the steps of:

providing:

(a) the conventional medical syringe comprising a hollow, elongated internal cylindrical surface which is contiguous to an open proximal end and t a distal end having a closed interior about an orifice through which fluid is transferred and a plunger and plunger stem assembly used to displace fluid within the barrel;

(b) the fluid pressure actuated valve comprising:

(1) a body for disposal within the barrel for dividing the barrel into a proximally disposed chamber wherein a fluid can be disposed and a distally disposed chamber wherein a fluid can be disposed, said body being cylindrically shaped and sized to be slideably displaced along the surface and function as syringe plunger while being so displaced;

(2) said body being made from two separate parts, each part being made from syringe plunger material which is incompressible, pliant and elastic, each of said parts comprising complimentary geometry by which the two parts are joined and sealed together to become a single unit comprising a common external surface which encloses a hollow internal cavity;

(3) each of said two separate body parts further comprising a medially disposed elongated hollow tube, which comprises a hollow communicating pathway, a pathway of one tube being sized and shaped to be to be inserted to sealingly and slideably engage the other tube, thereby forming an internal closed surface for said sealed hollow cavity, said cavity being filled with compressible matter disposed at a predetermined pressure when the two parts and associated tubes are joined and to also thereby provide a common pathway for fluid flow through the valve;

(4) a displaceable stopper comprising a bulging part sized and shaped to occlude said pathway which, in a first valve-closed-state is disposed to occlude the common pathway and in a second valve-open-state is displaced from the pathway to permit fluid flow there through; and (5) said body further comprising distal and proximal faces which interface with the distal and proximal chambers, respectively, said faces comprising thinned portions collectively providing distortable structure about said hollow cavity such that fluid pressure within said chambers at a predetermined amount greater than the predetermined pressure effects distortion of said proximal face of said body and concurrent displacement of said bulging part of said stopper part which is displaced from said pathway causing the valve to transition from the first valve-closed-state to the second valve open state permitting fluid flow through the valve;

displacing said valve into the syringe barrel to provide a proximal and a distal chamber;

filling each proximal and distal chamber with fluid to be dispensed separately;

displacing the plunger and plunger stem assembly to displace the valve thereby dispensing fluid from the distal chamber until contact with the closed interior if the barrel about the orifice;

increasing force upon the plunger stem assembly to increase pressure about the valve and thereby distort the distortable portion of the valve; and releasing force upon the plunger stem assembly permitting pressure to decrease about the valve and resultant expansion of the body to displace the additional elongated tube proximally, thereby displacing the stopper from the common pathway and opening the valve to permit fluid displacement there through only after pressure about the valve is decreased, thereby reducing likelihood of an inadvertent and undesired rate of fluid flow when the valve is opened.

7. A method for using a pressure actuated valve to divide a conventional medical syringe into two chambers for disparately storing fluids to be mixed in each chamber and for deliberately mixing the fluids then dispensing the mixture, the method comprising the steps of:

providing:
  (a) the conventional medical syringe comprising a hollow, elongated internal cylindrical surface which is contiguous to an open proximal end and t a distal end having a closed interior about an orifice through which fluid is transferred and a plunger and plunger stem assembly used to displace fluid within the barrel;
  (b) the fluid pressure actuated valve comprising:
    (1) a body for disposal within the barrel for dividing the barrel into a proximally disposed chamber wherein a diluent can be disposed and a distally disposed chamber wherein a drug to be mixed can be disposed, said body being cylindrically shaped and sized to be slideably displaced along the surface and function as syringe plunger while being so displaced;
    (2) said body being made from two separate parts, each part being made from syringe plunger material which is incompressible, pliant and elastic, each of said parts comprising complimentary geometry by which the two parts are joined and sealed together to become a single unit comprising a common external surface which encloses a hollow internal cavity;
    (3) each of said two separate body parts further comprising a medially disposed elongated hollow tube, which comprises a hollow communicating pathway, a pathway of one tube being sized and shaped to be to be inserted to sealingly and slideably engage the other tube, thereby forming an internal closed surface for said sealed hollow cavity, said cavity being filled with compressible matter disposed at a predetermined pressure when the two parts and associated tubes are joined and to also thereby provide a common pathway for fluid flow through the valve;
    (4) a displaceable stopper comprising a bulging part sized and shaped to occlude said pathway which, in a first valve-closed-state is disposed to occlude the common pathway and in a second valve-open-state is displaced from the pathway to permit fluid flow there through; and
    (5) said body further comprising distal and proximal faces which interface with the distal and proximal chambers, respectively, said faces comprising thinned portions collectively providing distortable structure about said hollow cavity such that fluid pressure within said chambers at a predetermined amount greater than the predetermined pressure effects distortion of said proximal face of said body and concurrent displacement of said bulging part of said stopper part which is displaced from said pathway causing the valve to transition from the first valve-closed-state to the second valve open state permitting fluid flow through the valve;

displacing said valve into the syringe barrel to provide a proximal and a distal chamber;

providing a predetermined amount of drug for mixing in the distal chamber;

providing diluent for mixing in the proximal chamber which remains disparate from the matter in the distal chamber until the valve is opened;

affixing a cap to close the orifice of the syringe, thereby providing a distal chamber which is closed at proximal and distal ends by said valve;

forcing the plunger and plunger stem by distal displacement into the syringe to increase pressure within the syringe to the predetermined amount above the predetermined pressure to open the valve; and while holding the syringe with the cap disposed downwardly, serially displacing the plunger and plunger stem assembly to pump liquid from the proximal chamber into the distal chamber for mixing of the matter and liquid.

8. A method according to claim 7 for providing and using a combination mixing and flush syringe comprising the additional steps of:

affixing an elongated stem to said stopper part which extends distally from the pressure actuated valve to be displaced as fluid is emptied from the distal chamber of the syringe;

disposing a displacement actuated valve to divide the proximal chamber into a medially disposed chamber and a more proximally disposed chamber, the displacement actuated valve being opened by displacement of a valve stem associated with the displacement actuated valve;

displacing the pressure actuated valve into direct communication with the displacement actuated valve as said pressure actuated valve is opened and diluent is displaced into the distal chamber from the medially disposed chamber; and removing the cap and fully dispensing fluid from the distal chamber of the syringe whereby said stopper part is displaced proximally relative to said body to contact and dislodge the valve stem of the displacement actuated valve, thereby opening the displacement actuated valve for subsequent dispensing of fluid from the more proximal chamber.

* * * * *